(12) United States Patent
Fitzgerald

(10) Patent No.: US 7,288,078 B2
(45) Date of Patent: Oct. 30, 2007

(54) SPRING LOADED AUTOMATIC RETRACTABLE NEEDLE SYRINGE

(75) Inventor: Lisa M. Fitzgerald, Sarasota, FL (US)

(73) Assignee: P. Rowan Smith, Jr., Houston, TX (US)

( * ) Notice: Subject to any disclaimer, the term of this patent is extended or adjusted under 35 U.S.C. 154(b) by 618 days.

(21) Appl. No.: 10/822,268

(22) Filed: Apr. 12, 2004

(65) Prior Publication Data

US 2005/0228344 A1    Oct. 13, 2005

(51) Int. Cl.
*A61M 5/00*    (2006.01)
*A61M 5/32*    (2006.01)

(52) U.S. Cl. .................. 604/110; 604/198; 604/263

(58) Field of Classification Search ........... 604/110, 604/198, 194–6, 192, 263
See application file for complete search history.

(56) References Cited

U.S. PATENT DOCUMENTS

| | | | |
|---|---|---|---|
| 4,747,831 A | | 5/1988 | Kulli |
| 5,112,316 A | | 5/1992 | Venturini |
| 5,167,641 A | * | 12/1992 | Schmitz .................. 604/196 |
| 5,232,457 A | * | 8/1993 | Grim ...................... 604/195 |
| 5,360,409 A | * | 11/1994 | Boyd et al. ............. 604/198 |
| 5,423,758 A | * | 6/1995 | Shaw ...................... 604/110 |
| 5,885,257 A | | 3/1999 | Badger |
| 6,589,209 B1 | * | 7/2003 | Dysarz ................... 604/110 |
| 7,090,656 B1 | * | 8/2006 | Botich et al. ........... 604/110 |

* cited by examiner

*Primary Examiner*—Kevin C. Sirmons
*Assistant Examiner*—Andrew Gilbert
(74) *Attorney, Agent, or Firm*—Richard L. Moseley

(57) ABSTRACT

A spring loaded retractable needle syringe comprising a body, a central tube coaxially mounted within said body, a needle carrier and needle slidably mounted within said central tube, a spring mounted within said central tube to bias said needle carrier and needle into said central tube, means for sliding said needle carrier and needle within said central tube to compress said spring and expose said needle, means for retaining said needle carrier and needle in the exposed position against the biasing force of said spring, and means for releasing the needle carrier and needle such that said needle carrier and needle are retracted into said central tube.

2 Claims, 7 Drawing Sheets

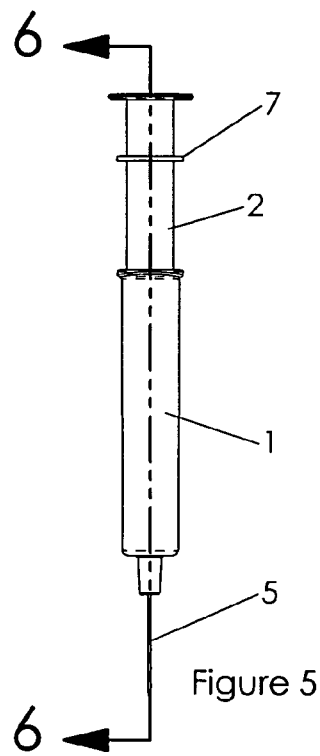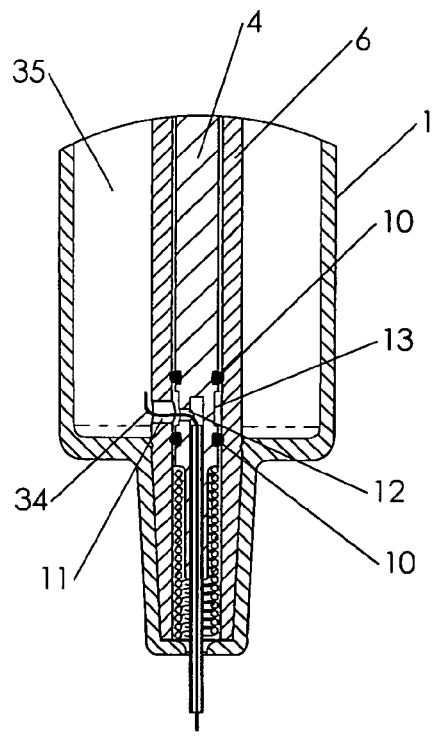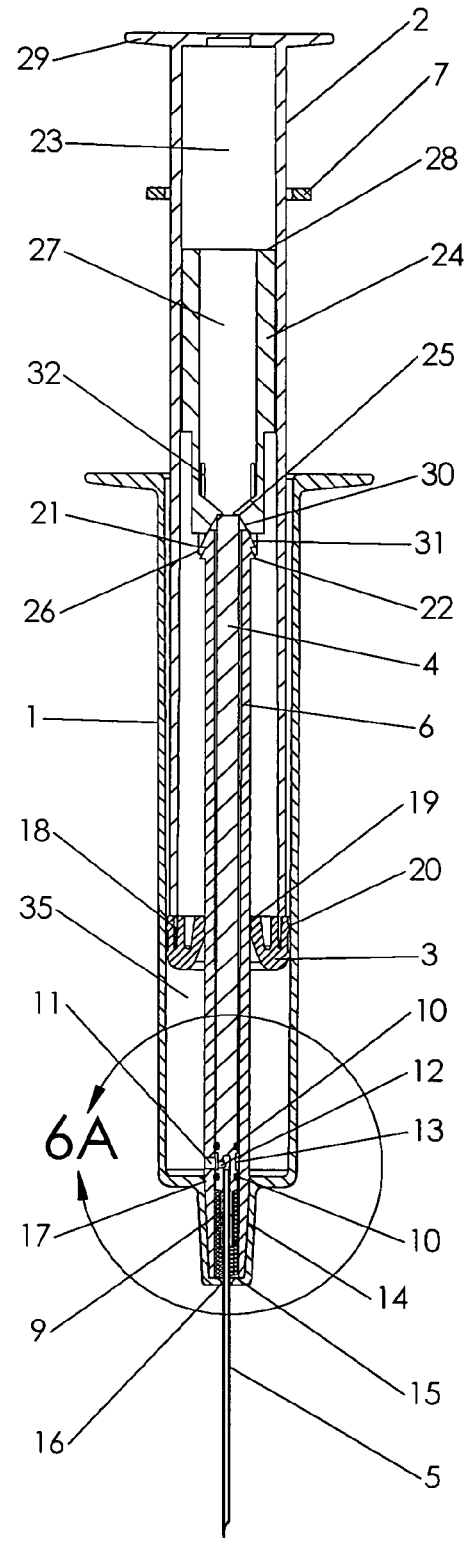
Figure 5
Figure 6A
Figure 6

SPRING LOADED AUTOMATIC RETRACTABLE NEEDLE SYRINGE

BACKGROUND OF THE INVENTION

1. Field of the Invention

The present invention relates to a retractable needle safety syringe in which the needle may be withdrawn into the barrel of the syringe after use. More particularly the invention relates to a retractable needle syringe wherein the plunger need not be connected to the needle or its carrier for the retraction. Most particularly the invention relates to a retractable needle syringe wherein the needle carrier is spring loaded so that it may be automatically retracted into the syringe barrel after use.

2. Related Art

Due to the recent advent of the AIDS virus, which may be contracted by contaminated hypodermic syringes, there have been several retractable needle hypodermic syringes invented and patented. The retraction of the needle into the barrel of the syringe after use reduces the risk of "needle prick", or the accidental pricking of the person giving the injection after the syringe has been used.

Some of the recently patented retractable needle syringes include U.S. Pat. No. 4,692,156 (Haller); U.S. Pat. No. 4,675,005 (DeLuccia); U.S. Pat. No. 4,747,830 (Gloyer, et al); U.S. Pat. No. 4,790,822 and U.S. Pat. No. 4,950,251. All of the syringes disclosed include a hypodermic needle mounted on a carrier which is slidable in the barrel. The plunger is locked to this carrier after the injection has been given and is withdrawn up into the barrel by withdrawal of the plunger. The simplest mechanism for locking the plunger to the carrier is disclosed as a projection on the lower end of the plunger which engages through an opening in the upper end of the carrier.

One disadvantage of the above syringes is that the locking mechanism takes up some space in the barrel of the syringe and may prevent all of the measured liquid from being ejected by the plunger. This problem is exacerbated in the very small syringes such as the 1 cc tuberculin type. The liquid left in the barrel may be a substantial portion of the measured dose. In addition the narrowness of the barrel of the 1 cc syringe makes it difficult to design a needle carrier and locking mechanism that will fit in the barrel without enlarging the diameter so much as to make the calibration useless.

Venturini in U.S. Pat. No. 5,112,316 discloses a syringe similar to the retractable needle syringes described above except Venturini adds a spring outside the upper end of the syringe between the finger flange on the top of the barrel and the bottom surface of a projection at the top of the plunger to retract the plunger into the barrel after it has been locked onto the needle carrier. Venturini suffers the same draw backs because the plunger must still be locked to the needle carrier.

SUMMARY OF THE INVENTION

The present invention provides a syringe which allows the needle to retract into a safe position inside the barrel or syringe body after use to prevent needle pricks to the user. In the initial state or unused position the needle is held fully captive by means of a spring and protected by a center tube which eliminates the need for a needle cap. A safety ring on the plunger holds the needle in the initial safe position. This ring is broken from the plunger by pressure on the plunger thus requiring only one hand to extend the needle for use. After use the needle is retracted into body by means of a spring. Again, only one hand operation is required to trigger the retraction by means of a second aggressive push on the plunger. A locking cap is provided which covers the open end of the body making a sealed assembly for disposal.

Briefly, the invention is spring loaded retractable needle syringe comprising a body, a central tube coaxially mounted within said body, a needle carrier and needle slidably mounted within said central tube, a spring mounted within said central tube to bias said needle carrier and needle into said central tube, means for sliding said needle carrier and needle within said central tube to compress said spring and expose said needle, means for retaining said needle carrier and needle in the exposed position against the biasing force of said spring, and means for releasing the needle carrier and needle such that said needle carrier and needle are retracted into said central tube.

BRIEF DESCRIPTION OF THE DRAWING

FIG. 5 is a side plan view of the device with the needle in the extended position.

FIG. 6 is a side plan view of in cross section taken along line 6-6 of FIG. 5.

FIG. 6A is an enlarged cross sectional view of the area circled in FIG. 6.

DESCRIPTION OF THE PREFERRED EMBODIMENTS

Figure 1:
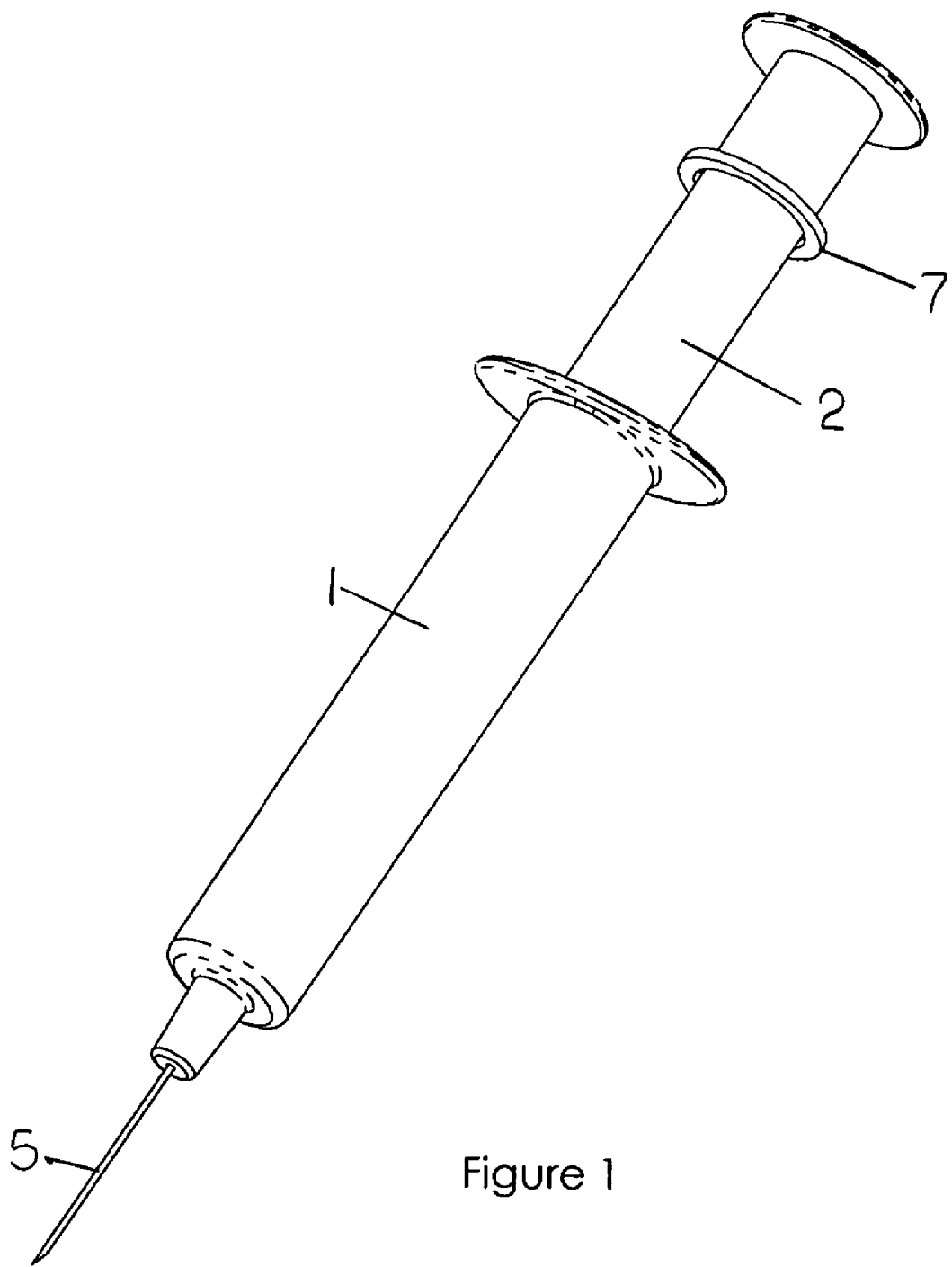
FIG. 1 is an isometric view of device of the present invention.

For a detailed description of the preferred embodiment the reader is referred to the appended figures in which like components are given like numerals for ease of reference.

For quick reference all of the reference numerals are listed in Table I below and their corresponding parts identified with the figures in which the parts are identified. The parts may be shown in other figures but are identified by the reference numerals in the listed figures only.

TABLE I

| Ref. No. | Description | Identified in Figure Number: |
|---|---|---|
| 1 | Syringe Body | 1-6, 6A, 8, 8A, 10-12, 12A |
| 2 | Plunger | 1-6, 8, 8A, 10, 11 |
| 3 | Plunger Seal | 3, 6, 8, 10, 11 |
| 4 | Needle Carrier | 3, 6, 6A, 8, 8A, 10, 11 |
| 5 | Needle | 1, 3, 5, 6, 8, 11 |
| 6 | Center Tube | 3, 6, 6A, 8, 8A, 10, 11, 12A |
| 7 | Plunger Retaining Ring | 1-6, 8, 10 |

TABLE I-continued

| Ref. No. | Description | Identified in Figure Number: |
|---|---|---|
| 8 | Ring Snap-off Tab | 3, 4 |
| 9 | Spring | 3, 6, 8, 10, 11 |
| 10 | O-ring | 3, 6, 6A, 8, 10, 11 |
| 11 | Center Tube Flow Aperture | 3, 6, 6A, 8, 10, 11 |
| 12 | Needle Carrier Flow Aperture | 3, 6, 6A, 8, 10 |
| 13 | Needle Carrier Flow Ring | 3, 6, 6A, 8, 10, 11 |
| 14 | Luer Seal | 3, 6, 8, 10 |
| 15 | Spring Retainer Surface | 3, 6, 8, 10 |
| 16 | Needle Aperture | 3, 6, 8, 10, 12A |
| 17 | Center Tube Retaining Ring | 3, 6, 10, 11 |
| 18 | Seal Retaining Finger | 3, 6, 8, 10 |
| 19 | Center Tube Wiper | 3, 6, 8, 10 |
| 20 | Syringe Body Wiper | 3, 6, 8, 10 |
| 21 | Needle Retainer Notch | 3, 6, 8, 8A, 10, 11 |
| 22 | Needle Release Notch | 3, 6, 8, 8A, 10, 11 |
| 23 | Plunger Inner Cavity | 3, 6, 8, 8A, 10 |
| 24 | Needle Carrier Actuator | 3, 6, 8, 8A, 10, 11 |
| 25 | Needle Carrier Actuator Retainer Latch | 3, 6, 8, 8A, 10 |
| 26 | Needle Carrier Actuator Retainer Snap | 3, 6, 8, 8A, 10, 11 |
| 27 | Needle Carrier Actuator Inner Cavity | 3, 6, 8A, 10 |
| 28 | Needle Carrier Actuator Push Surface | 3, 6, 8, 10 |
| 29 | Plunger Push Surface | 3, 6, 8, 10 |
| 30 | Needle Carrier Actuator Latch Release Surface | 3, 6, 8, 8A, 10 |
| 31 | Center Tube Release Cone | 3, 6, 8, 8A, 10, 11 |
| 32 | Needle Carrier Actuator Release Slot | 3, 6, 8, 8A, 10, 11 |
| 33 | Center Tube Inner Cavity | 3, 10 |
| 34 | Flow Path | 6A |
| 35 | Syringe Body Inner Cavity | 3, 6, 6A |
| 36 | Safety Cap | 12, 12A |
| 37 | Cap Snap Retainer | 12A |

Figure 2:
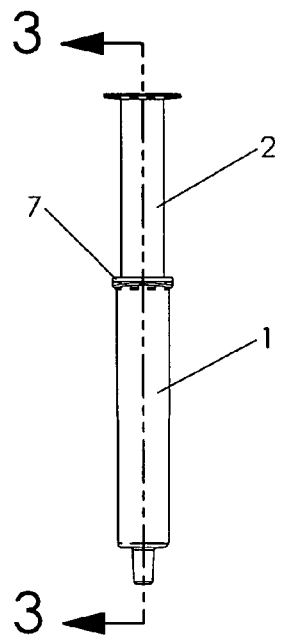
FIG. 2 is a side plan view of the device in the initial state.
Figure 4:
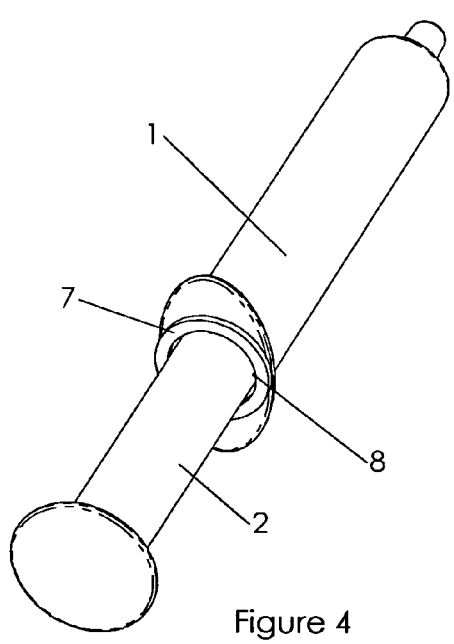
FIG. 4 is a second isometric view of the device from an angle different than that of FIG. 1.
Figure 3:
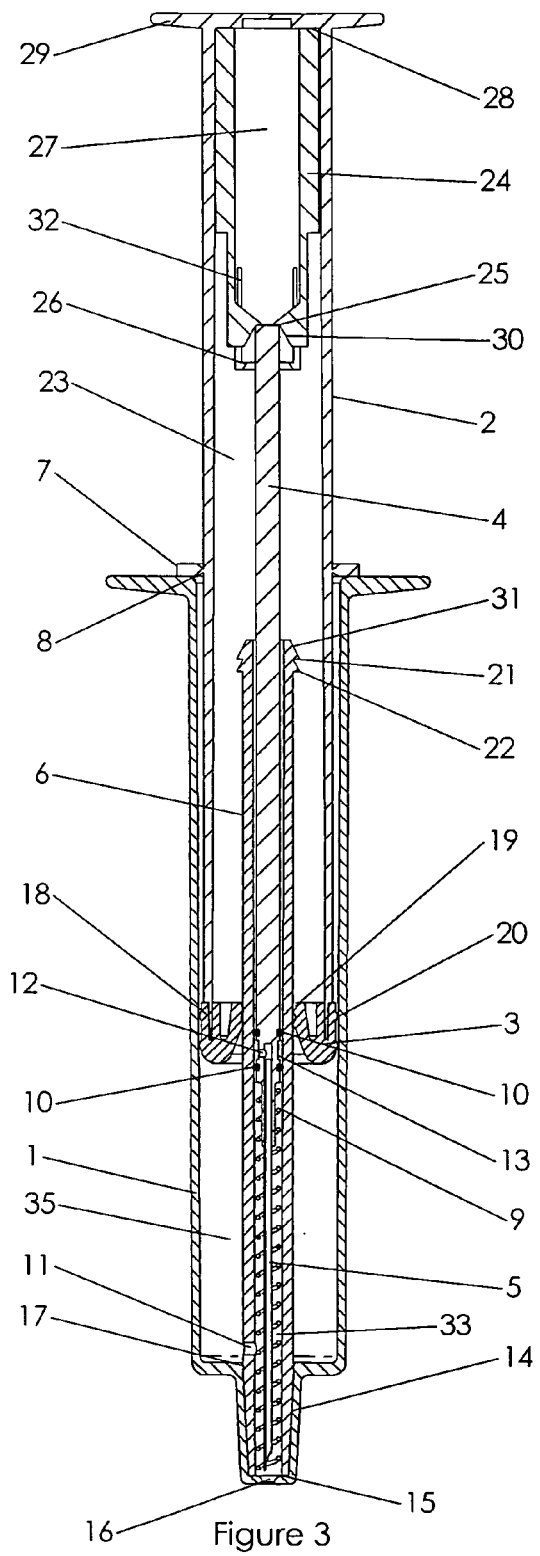
FIG. 3 is a side plan view in cross section taken along line 3-3 of FIG. 2.
Figure 7:
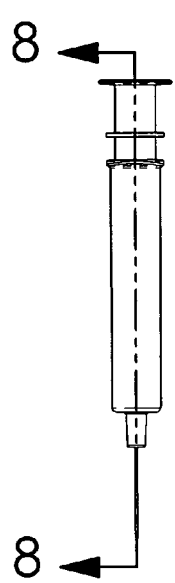
FIG. 7 is a side plan view of the device in the release phase of operation.

Referring first to FIGS. 2-4 the device is shown in its initial state, or as shipped with the needle 5 inside the body 1. The needle 5 is molded within the needle carrier 4 and is captured in the center tube inner cavity 33. The needle carrier 4 is biased by spring 9 against spring retaining surface 15 to maintain this position with the needle 5 fully retracted into the center tube 6. The center tube 6 is held to the syringe body 1 by means of a snap-in center tube retaining ring 17 and the luer seal 14. The needle carrier actuator 24, inside the plunger inner cavity 23, rests on top of the needle carrier 4 by the needle carrier actuator retainer latch 25. The plunger 2 rests on the needle carrier actuator 24 by means of the needle carrier actuator push surface 28. As shown in FIG. 4 plunger 2 is held in position by the plunger retaining ring 7 and a plurality of ring snap-off tabs 8.

Referring now to FIGS. 5 and 6 the initial exposing of the needle is disclosed. To expose the needle 5 for use, the plunger 2 is depressed into the syringe body 1 by applying pressure to the plunger push surface 29, thereby breaking the snap-off tabs 8 on plunger retaining ring 7. This allows the needle carrier actuator 24 to be driven toward the distal end in tandem with the needle carrier actuator 24 and the needle carrier 4 and needle 5 by means of the needle carrier actuator retainer latch 25, until the needle carrier actuator retainer snap 26 on the needle carrier actuator 24 engages the needle retainer notch 21 on the center tube 6. The needle carrier actuator retainer latch 25 drives the needle 5 through the needle aperture 16 and the needle carrier actuator retainer snap 26 locks the needle 5 in the extended position as required for an injection.

Figure 11:
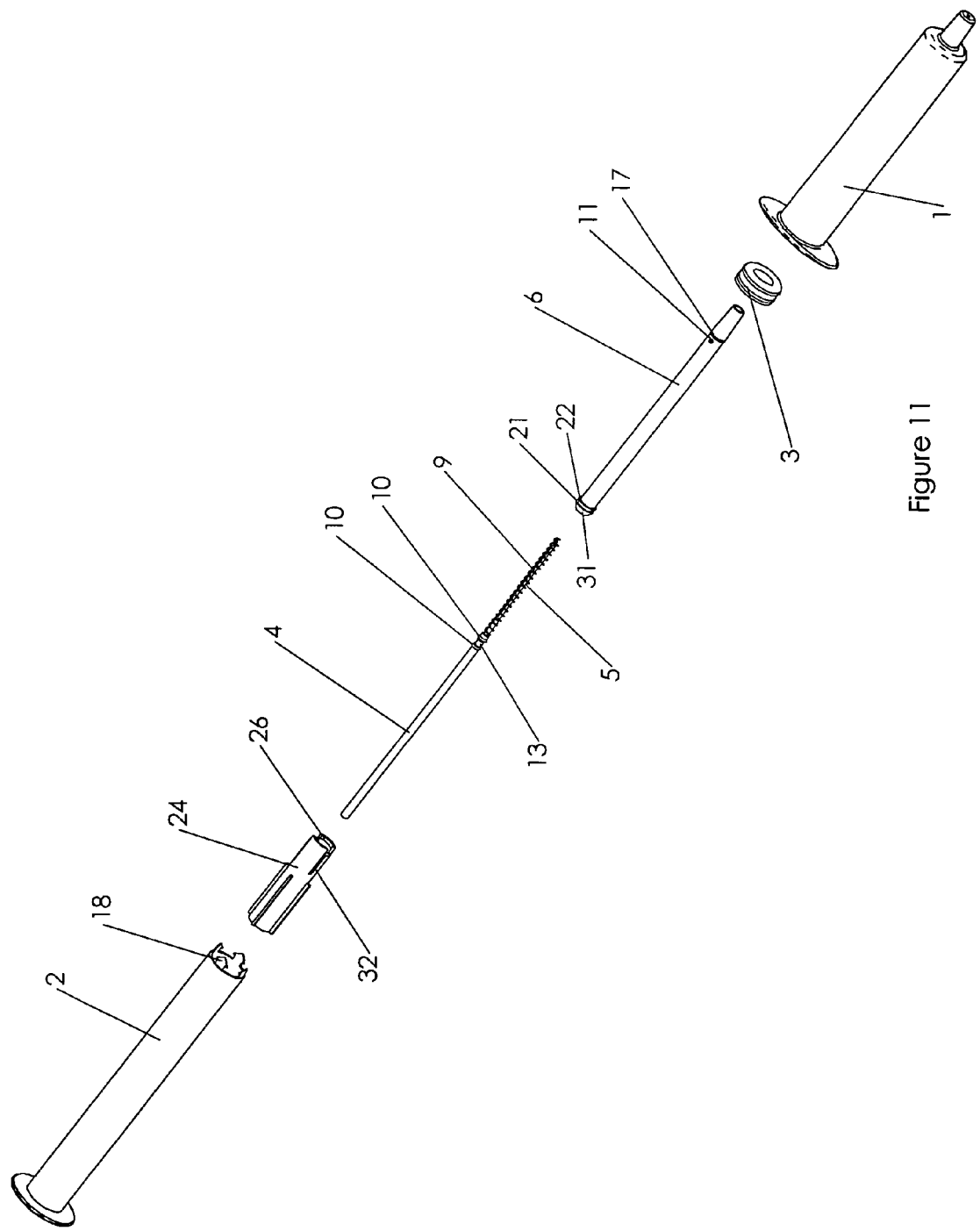
FIG. 11 is an exploded view of the device.

Referring to FIG. 6A, when the needle 5 is in the extended position the needle carrier flow aperture 12 in the needle carrier 4 aligns with the center tube aperture 11 in the center tube. This enables the flow path 34 confined by o-ring 10 located on either side of the needle carrier flow aperture 12 on needle carrier 4. The needle carrier flow ring 13 allows radial movement of the needle carrier 4 relative to the center tube 6 to prevent compromising the flow path 34. Referring again to FIG. 6, the injectable fluid resides in the syringe body inner cavity until plunger 2 is depressed, pushing the plunger seal 3 towards the distal end of the syringe body 1. Plunger seal 3 seals against the inner wall of the syringe body 1 by means of the syringe body wiper 20, and the against the center tube 6 by means of the center tube wiper 19. This sealing action forms a seal to expel the fluid in the syringe body inner cavity 35 along the flow path 34 and through needle 5. The plunger seal 3 is held to the plunger 2 by a plurality of seal retaining fingers 18 as best shown in FIG. 11. Note also that the spring 9 is isolated from the injection fluid by the o-rings 10 at all times. The flow path 34 enters the needle carrier aperture 12 and flows through the needle 5 without contacting the spring 9.

Figure 8A:
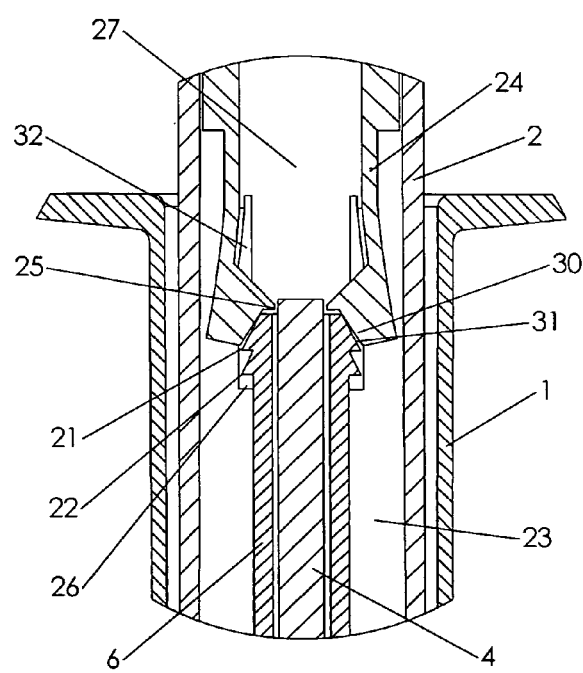
FIG. 8A is an enlarged cross sectional view of the area circled in FIG. 8.
Figure 8:
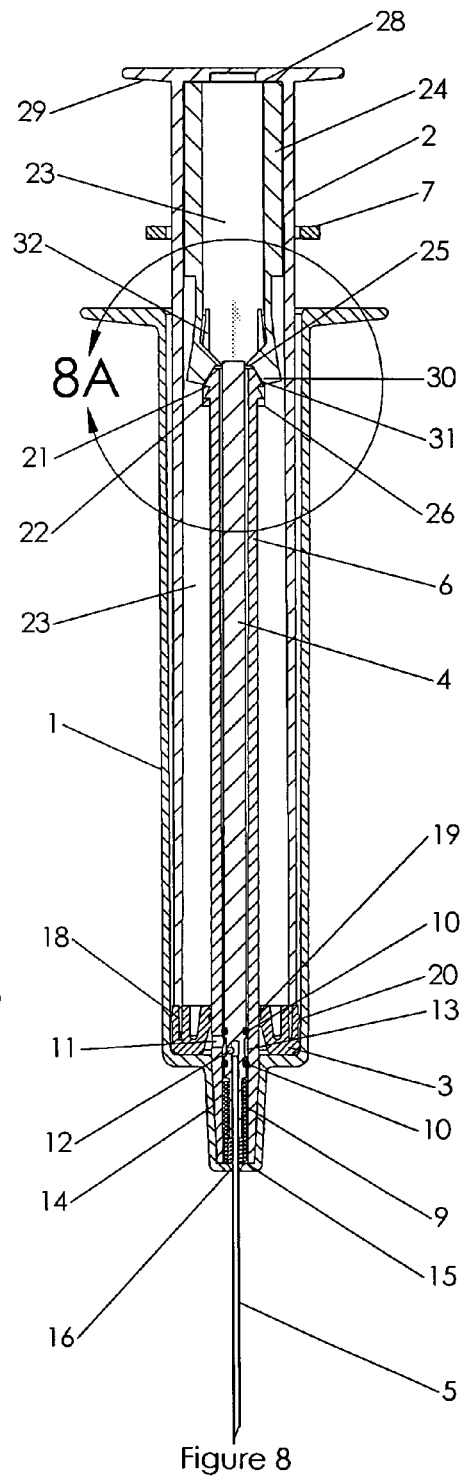
FIG. 8 is a side plan view in cross section taken along line 8-8 of FIG. 7.
Figure 9:
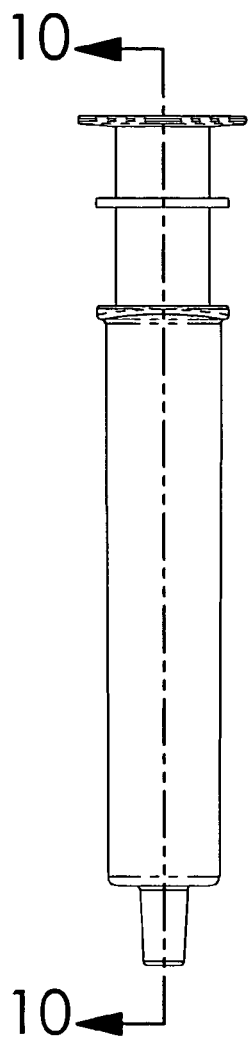
FIG. 9 is a side plan view of the device with the needle in the safe stowed position after use.
Figure 10:
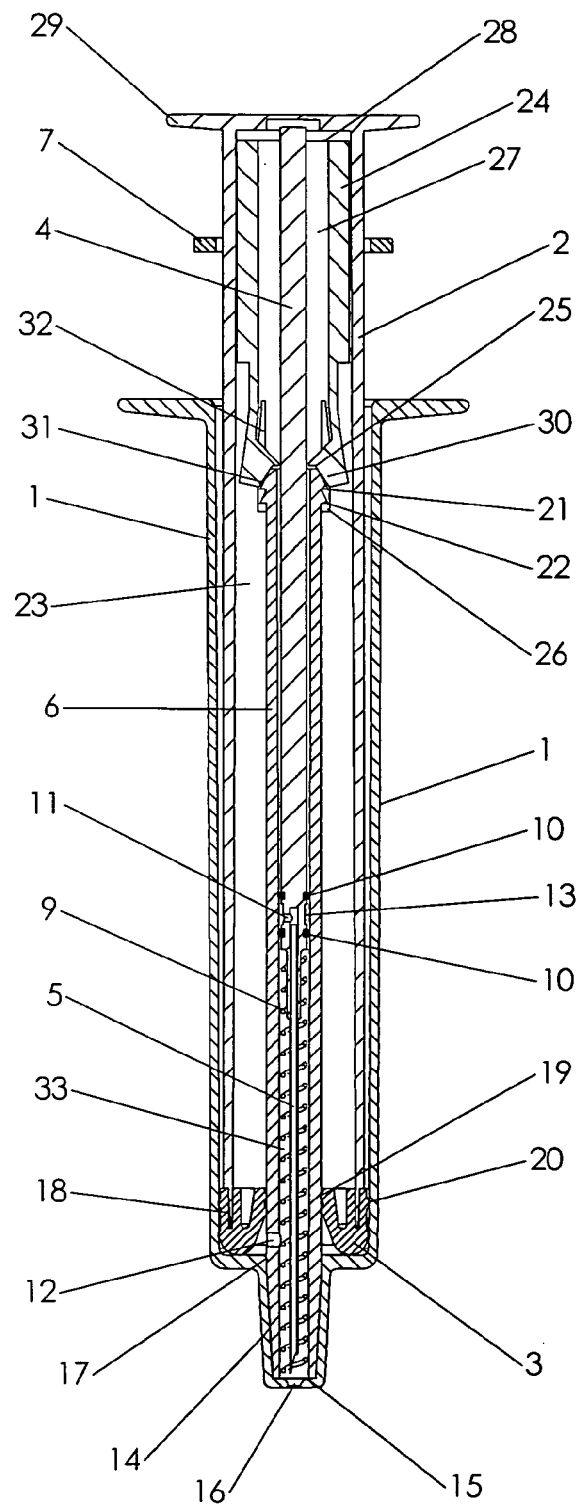
FIG. 10 is a side plan view in cross section taken along line 10-10 in FIG. 9.

Referring now to FIG. 8, after the injection is administered, the plunger 2 is depressed further into the syringe body 1 causing the plunger seal to be compressed between the plunger 2 and the distal inside surface of the syringe body 1. This allows for further movement of the needle carrier actuator 24 as is it contacted at the needle carrier push surface 28 by the inside surface of the plunger 2. As shown in FIG. 8A, this movement causes the needle carrier actuator retainer snap 26 to engage the needle release notch 22 on the center tube 2. In this position the needle carrier actuator latch release surface 30 contacts the center tube release cone 31. This in turn causes the needle carrier actuator retainer latch 25 to be spread apart and away from the top surface of the needle carrier 4, relieved by the needle carrier actuator release slot 32, allowing room for the needle carrier 4 to slide by the needle carrier actuator retainer latch 25 as it is biases upward by spring 9 against spring retaining surface 15, and into the needle carrier actuator inner cavity 27. As shown in FIG. 10, when the needle carrier 4 is fully inserted into the needle carrier actuator inner cavity 27, the needle 5 is fully encased by the center tube 6 and the administrator is safe from needle pricks. The plunger 2 remains with the assembly and captures the needle carrier 4 and needle actuator 24.

Figures 12, 12A:
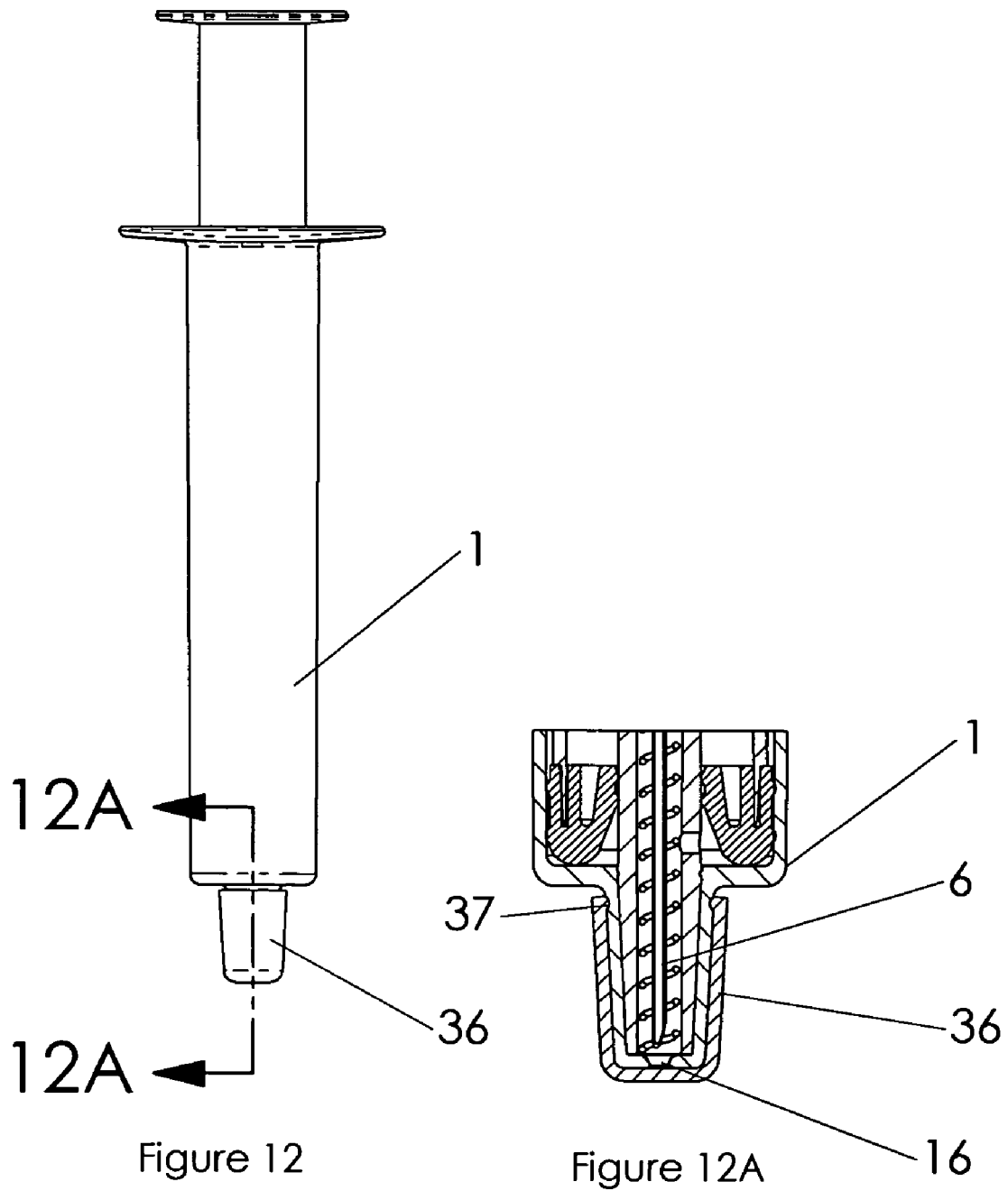
FIG. 12 is a side plan view of the device with a safety cap in place.
FIG. 12A is an enlarged cross sectional view taken along line 12A-12A in FIG. 12.

Finally, as shown in FIGS. 12 and 12A a safe cap 36 is pressed on the syringe body to completely seal the needle aperture 16. The safety cap 36 snaps into a cap snap retainer groove 37 on the syringe body and is unremovable.

The foregoing description of the invention has been directed to a particular preferred embodiment of the present invention for the purposes of explanation and illustration. It will be apparent to those skilled in the art that many modifications and changes in the apparatus may be made without departing from the scope and spirit of the invention. It is therefore intended that the following claims cover all equivalent modifications and variations as fall within the scope of the invention as defined by the claims.

The invention claimed is:

1. A spring loaded retractable needle syringe comprising:
   (a) a body having a proximal end and a distal end;
   (b) central tube coaxially mounted within said body, said central tube having a proximal end and a distal end and a central tube aperture at the distal end;

(c) a hollow slidable plunger mounted through said proximal end and in sealing engagement with said body and said central tube;

(d) a needle carrier and needle slidably mounted within said central tube, said needle carrier having a proximal end and a distal end;

(e) a spring mounted within said central tube at the distal end to bias said needle carrier and needle within said central tube;

(f) a needle carrier retainer snap mounted on the proximal end of said needle carrier;

(g) a needle carrier retainer notch mounted on said central tube engageable with said needle carrier retainer snap when said needle is exposed through the distal end of said body to retain said needle carrier and needle in the exposed position;

(h) a needle carrier flow aperture through said needle carrier to the proximal end of said needle within said needle carrier, said needle carrier flow aperture alignable with said center tube aperture when said needle is in the exposed position;

(i) a needle carrier actuator mounted on the distal end of said plunger;

(j) a needle release notch mounted near the proximal end of said center tube;

(k) a release cone mounted on the proximal of said center tube; and (l) a needle carrier retainer release latch mounted on the distal of said plunger engageable with said release cone to be spread apart and release the needle carrier from its exposed position and retract the needle carrier into the plunger and the needle into the center tube.

2. The spring loaded retractable needle syringe according to claim 1 further comprising a safety cap adapted to fit over the distal end of said body after said needle carrier and needle has been retracted.

* * * * *